United States Patent
Couvillon, Jr.

(10) Patent No.: US 7,967,759 B2
(45) Date of Patent: Jun. 28, 2011

(54) ENDOSCOPIC SYSTEM WITH INTEGRATED PATIENT RESPIRATORY STATUS INDICATOR

(75) Inventor: Lucien Alfred Couvillon, Jr., Concord, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 924 days.

(21) Appl. No.: 11/336,688

(22) Filed: Jan. 19, 2006

(65) Prior Publication Data
US 2007/0167683 A1  Jul. 19, 2007

(51) Int. Cl.
*A61B 5/08* (2006.01)

(52) U.S. Cl. ........ 600/529; 600/484; 600/531; 600/532; 600/533; 600/534; 600/535; 600/536; 600/537; 600/538; 73/23.3; 128/204.23

(58) Field of Classification Search .................. 600/484, 600/529, 531–538; 73/23.3; 128/204.22, 128/204.23
See application file for complete search history.

(56) References Cited

U.S. PATENT DOCUMENTS

| | | | |
|---|---|---|---|
| 3,266,059 A | 8/1966 | Stelle | |
| 3,470,876 A | 10/1969 | Barchilon | |
| 3,572,325 A | 3/1971 | Bazell et al. | |
| 3,581,738 A | 6/1971 | Moore | |
| 3,927,670 A | * 12/1975 | Turney et al. | 600/532 |
| 4,108,211 A | 8/1978 | Tanaka | |
| 4,286,585 A | 9/1981 | Ogawa | |
| 4,294,162 A | 10/1981 | Fowler et al. | |
| 4,315,309 A | 2/1982 | Coli | |
| 4,351,323 A | 9/1982 | Ouchi et al. | |
| 4,423,739 A | 1/1984 | Passaro et al. | |
| 4,425,113 A | 1/1984 | Bilstad | |
| 4,432,349 A | 2/1984 | Oshiro | |
| 4,471,766 A | 9/1984 | Terayama | |
| 4,473,841 A | 9/1984 | Murakoshi et al. | |

(Continued)

FOREIGN PATENT DOCUMENTS
EP  0 689 851 A1  1/1996
(Continued)

OTHER PUBLICATIONS
Kodali, B.S., "Physics of Capnography," www.capnography.com, Jan. 2004, <http://www.capnography.com/Physics/Physicsphysical.htm>[retrieved Jun. 19, 2004].
(Continued)

*Primary Examiner* — John P Leubecker
*Assistant Examiner* — Samuel Candler
(74) *Attorney, Agent, or Firm* — Finnegan, Henderson, Farabow, Garrett & Dunner

(57) ABSTRACT

The system 10 includes an endoscopic probe 20 and an expired air sampling device 24 functionally connected to a control console 28. In use, the endoscopic probe 20 is routed through a body lumen of a patient to, for example, visualize a selected region of a patient's body. As the endoscopic probe 20 is routed through the body lumens, the expired air sampling device 24 collects expired air from the patient, generates signals indicative of patient respiratory status, and outputs the generated signals to the control console 28. The control console 28 processes the signals and monitors the respiratory status of the patient. If the respiratory status of the patient changes based on the processed signals of the expired air sampling device 24, the control console 28 may output an audible or visual alert signal.

17 Claims, 6 Drawing Sheets

U.S. PATENT DOCUMENTS

| | | | |
|---|---|---|---|
| 4,488,039 A | 12/1984 | Sato et al. | |
| 4,491,865 A | 1/1985 | Danna et al. | |
| 4,495,134 A | 1/1985 | Ouchi et al. | |
| 4,499,895 A | 2/1985 | Takayama | |
| 4,513,235 A | 4/1985 | Acklam et al. | |
| 4,515,444 A | 5/1985 | Prescott et al. | |
| 4,516,063 A | 5/1985 | Kaye et al. | |
| 4,519,391 A | 5/1985 | Murakoshi | |
| 4,559,928 A | 12/1985 | Takayama | |
| 4,573,450 A | 3/1986 | Arakawa | |
| 4,580,210 A | 4/1986 | Nordstrom | |
| 4,586,923 A | 5/1986 | Gould et al. | |
| 4,615,330 A | 10/1986 | Nagasaki et al. | |
| 4,616,630 A | 10/1986 | Arakawa | |
| 4,617,915 A | 10/1986 | Arakawa | |
| 4,621,618 A | 11/1986 | Omagari et al. | |
| 4,625,714 A | 12/1986 | Toyota | |
| 4,631,582 A | 12/1986 | Nagasaki et al. | |
| 4,633,303 A | 12/1986 | Nagasaki et al. | |
| 4,633,304 A | 12/1986 | Nagasaki | |
| 4,643,170 A | 2/1987 | Miyazaki et al. | |
| 4,646,723 A | 3/1987 | Arakawa | |
| 4,649,904 A | 3/1987 | Krauter et al. | |
| 4,651,202 A | 3/1987 | Arakawa | |
| 4,652,093 A | 3/1987 | Stephen et al. | |
| 4,652,916 A | 3/1987 | Suzaki et al. | |
| 4,654,701 A | 3/1987 | Yabe | |
| RE32,421 E | 5/1987 | Hattori | |
| 4,662,725 A | 5/1987 | Nisioka | |
| 4,663,657 A | 5/1987 | Nagasaki et al. | |
| 4,667,655 A | 5/1987 | Ogiu et al. | |
| 4,674,844 A | 6/1987 | Nishioka et al. | |
| 4,686,963 A | 8/1987 | Cohen et al. | |
| 4,697,210 A | 9/1987 | Toyota et al. | |
| 4,700,693 A | 10/1987 | Lia et al. | |
| 4,714,075 A | 12/1987 | Krauter et al. | |
| 4,716,457 A | 12/1987 | Matsuo | |
| 4,719,508 A | 1/1988 | Sasaki et al. | |
| 4,727,417 A | 2/1988 | Kanno et al. | |
| 4,727,418 A | 2/1988 | Kato et al. | |
| 4,745,470 A | 5/1988 | Yabe et al. | |
| 4,745,471 A | 5/1988 | Takamura et al. | |
| 4,746,974 A | 5/1988 | Matsuo | |
| 4,748,970 A | 6/1988 | Nakajima | |
| 4,755,029 A | 7/1988 | Okobe | |
| 4,762,119 A | 8/1988 | Allred et al. | |
| 4,765,312 A | 8/1988 | Sasa et al. | |
| 4,766,489 A | 8/1988 | Kato | |
| 4,787,369 A | 11/1988 | Allred et al. | |
| 4,790,294 A | 12/1988 | Allred et al. | |
| 4,794,913 A | 1/1989 | Shimonaka et al. | |
| 4,796,607 A | 1/1989 | Allred et al. | |
| 4,800,869 A | 1/1989 | Nakajima | |
| 4,805,596 A | 2/1989 | Hatori | |
| 4,806,011 A | 2/1989 | Bettinger | |
| 4,819,065 A | 4/1989 | Eino | |
| 4,819,077 A | 4/1989 | Kikuchi et al. | |
| 4,821,116 A | 4/1989 | Nagasaki et al. | |
| 4,824,225 A | 4/1989 | Nishioka | |
| 4,831,437 A | 5/1989 | Nishioka et al. | |
| 4,836,187 A | 6/1989 | Iwakoshi et al. | |
| 4,844,052 A | 7/1989 | Iwakoshi et al. | |
| 4,845,553 A | 7/1989 | Konomura et al. | |
| 4,845,555 A | 7/1989 | Yabe et al. | |
| 4,847,694 A | 7/1989 | Nishihara | |
| 4,853,772 A | 8/1989 | Kikuchi | |
| 4,860,731 A | 8/1989 | Matsuura | |
| 4,867,546 A | 9/1989 | Nishioka et al. | |
| 4,868,647 A | 9/1989 | Uehara et al. | |
| 4,869,237 A | 9/1989 | Eino et al. | |
| 4,873,965 A | 10/1989 | Danieli | |
| 4,875,468 A | 10/1989 | Krauter et al. | |
| 4,877,314 A | 10/1989 | Kanamori | |
| 4,882,623 A | 11/1989 | Uchikubo | |
| 4,884,134 A | 11/1989 | Tsuji et al. | |
| 4,885,634 A | 12/1989 | Yabe | |
| 4,890,159 A | 12/1989 | Ogiu | |
| 4,894,715 A | 1/1990 | Uchikubo et al. | |
| 4,895,431 A | 1/1990 | Tsujiuchi et al. | |
| 4,899,731 A | 2/1990 | Takayama et al. | |
| 4,899,732 A | 2/1990 | Cohen | |
| 4,899,787 A | 2/1990 | Ouchi et al. | |
| 4,905,666 A | 3/1990 | Fukuda | |
| 4,907,166 A * | 3/1990 | Corenman et al. | 702/30 |
| 4,918,521 A | 4/1990 | Yabe et al. | |
| 4,919,112 A | 4/1990 | Siegmund | |
| 4,919,114 A | 4/1990 | Miyazaki | |
| 4,920,980 A | 5/1990 | Jackowski | |
| 4,928,172 A | 5/1990 | Uehara et al. | |
| 4,931,867 A | 6/1990 | Kikuchi | |
| 4,941,454 A | 7/1990 | Wood et al. | |
| 4,941,456 A | 7/1990 | Wood et al. | |
| 4,951,134 A | 8/1990 | Nakasima et al. | |
| 4,951,135 A | 8/1990 | Sasagawa et al. | |
| 4,952,040 A | 8/1990 | Igarashi | |
| 4,958,075 A | 9/1990 | Mace et al. | |
| 4,960,127 A | 10/1990 | Noce et al. | |
| 4,961,110 A | 10/1990 | Nakamura | |
| 4,967,269 A | 10/1990 | Sasagawa et al. | |
| 4,971,034 A | 11/1990 | Doi et al. | |
| 4,973,311 A | 11/1990 | Iwakoshi et al. | |
| 4,979,497 A | 12/1990 | Matsuura et al. | |
| 4,982,725 A | 1/1991 | Hibino et al. | |
| 4,984,878 A | 1/1991 | Miyano | |
| 4,986,642 A | 1/1991 | Yokota et al. | |
| 4,987,884 A | 1/1991 | Nishioka et al. | |
| 4,989,075 A | 1/1991 | Ito | |
| 4,989,581 A | 2/1991 | Tamburrino et al. | |
| 4,996,974 A | 3/1991 | Ciarlei | |
| 4,996,975 A | 3/1991 | Nakamura | |
| 5,001,556 A | 3/1991 | Nakamura et al. | |
| 5,005,558 A | 4/1991 | Aomori | |
| 5,005,957 A | 4/1991 | Kanamori et al. | |
| 5,007,408 A | 4/1991 | Ieoka | |
| 5,018,509 A | 5/1991 | Suzuki et al. | |
| 5,022,382 A | 6/1991 | Ohshoki et al. | |
| 5,029,016 A | 7/1991 | Hiyama et al. | |
| 5,034,888 A | 7/1991 | Uehara et al. | |
| 5,040,069 A | 8/1991 | Matsumoto et al. | |
| RE33,689 E | 9/1991 | Nishioka et al. | |
| 5,045,935 A | 9/1991 | Kikuchi | |
| 5,049,989 A | 9/1991 | Tsuji | |
| 5,050,584 A | 9/1991 | Matsuura | |
| 5,050,974 A | 9/1991 | Takasugi et al. | |
| 5,056,503 A | 10/1991 | Nagasaki | |
| 5,061,994 A | 10/1991 | Takahashi | |
| 5,068,719 A | 11/1991 | Tsuji | |
| 5,069,220 A * | 12/1991 | Casparie et al. | 600/532 |
| 5,081,524 A | 1/1992 | Tsuruoka et al. | |
| 5,087,989 A | 2/1992 | Igarashi | |
| 5,110,645 A | 5/1992 | Matsumoto et al. | |
| 5,111,281 A | 5/1992 | Sekiguchi | |
| 5,111,306 A | 5/1992 | Kanno et al. | |
| 5,111,804 A | 5/1992 | Funakoshi | |
| 5,113,254 A | 5/1992 | Kanno et al. | |
| 5,119,238 A | 6/1992 | Igarashi | |
| 5,129,401 A * | 7/1992 | Corenman et al. | 600/529 |
| 5,131,393 A | 7/1992 | Ishiguro et al. | |
| 5,137,013 A | 8/1992 | Chiba et al. | |
| 5,140,265 A | 8/1992 | Sakiyama et al. | |
| 5,159,446 A | 10/1992 | Hibino et al. | |
| 5,159,934 A | 11/1992 | Hoberman | |
| 5,170,775 A | 12/1992 | Tagami | |
| 5,172,225 A | 12/1992 | Takahashi et al. | |
| 5,174,293 A | 12/1992 | Hagiwara | |
| 5,176,629 A | 1/1993 | Kullas et al. | |
| 5,191,878 A | 3/1993 | Iida et al. | |
| 5,198,931 A | 3/1993 | Igarashi | |
| 5,201,908 A | 4/1993 | Jones | |
| 5,208,702 A | 5/1993 | Shiraiwa | |
| 5,209,220 A | 5/1993 | Hiyama et al. | |
| 5,225,958 A | 7/1993 | Nakamura | |
| 5,228,356 A | 7/1993 | Chuang | |
| 5,243,416 A | 9/1993 | Nakazawa | |
| 5,243,967 A | 9/1993 | Hibino | |
| 5,257,628 A | 11/1993 | Ishiguro et al. | |
| 5,271,381 A | 12/1993 | Ailinger et al. | |

| | | |
|---|---|---|
| RE34,504 E | 1/1994 | Uehara et al. |
| 5,291,010 A | 3/1994 | Tsuji |
| 5,299,559 A | 4/1994 | Bruce et al. |
| 5,311,858 A | 5/1994 | Adair |
| 5,325,845 A | 7/1994 | Adair et al. |
| 5,331,551 A | 7/1994 | Tsuruoka et al. |
| 5,342,299 A | 8/1994 | Snoke et al. |
| 5,347,989 A | 9/1994 | Monroe et al. |
| 5,374,953 A | 12/1994 | Sasaki et al. |
| 5,379,757 A | 1/1995 | Hiyama et al. |
| 5,381,782 A | 1/1995 | DeLaRama et al. |
| 5,390,662 A | 2/1995 | Okada |
| 5,400,769 A | 3/1995 | Tanii et al. |
| 5,402,768 A | 4/1995 | Adair |
| 5,402,769 A | 4/1995 | Tsuji |
| 5,409,485 A | 4/1995 | Suda |
| 5,412,478 A | 5/1995 | Ishihara et al. |
| 5,418,649 A | 5/1995 | Igarashi |
| 5,420,644 A | 5/1995 | Watanabe |
| 5,431,645 A | 7/1995 | Smith et al. |
| 5,434,615 A | 7/1995 | Matumoto |
| 5,436,640 A | 7/1995 | Reeves |
| 5,436,767 A | 7/1995 | Suzuki et al. |
| 5,440,341 A | 8/1995 | Suzuki et al. |
| 5,445,160 A | 8/1995 | Culver et al. |
| 5,464,007 A | 11/1995 | Krauter et al. |
| 5,469,840 A | 11/1995 | Tanii et al. |
| 5,473,235 A | 12/1995 | Lance et al. |
| 5,482,029 A | 1/1996 | Sekiguchi et al. |
| 5,484,407 A | 1/1996 | Osypka |
| 5,485,316 A | 1/1996 | Mori et al. |
| 5,496,260 A | 3/1996 | Krauter et al. |
| 5,515,449 A | 5/1996 | Tsuruoka et al. |
| 5,518,501 A | 5/1996 | Oneda et al. |
| 5,543,831 A | 8/1996 | Tsuji et al. |
| 5,569,158 A | 10/1996 | Suzuki et al. |
| 5,569,159 A | 10/1996 | Anderson et al. |
| 5,586,262 A | 12/1996 | Komatsu et al. |
| 5,589,854 A | 12/1996 | Tsai |
| 5,591,202 A | 1/1997 | Slater et al. |
| 5,608,451 A | 3/1997 | Konno et al. |
| 5,619,380 A | 4/1997 | Ogasawara et al. |
| 5,622,528 A | 4/1997 | Hamano et al. |
| 5,631,695 A | 5/1997 | Nakamura et al. |
| 5,633,203 A | 5/1997 | Adair |
| 5,643,203 A | 7/1997 | Beiser et al. |
| 5,645,075 A | 7/1997 | Palmer et al. |
| 5,647,840 A | 7/1997 | D'Amelio et al. |
| 5,658,238 A | 8/1997 | Suzuki et al. |
| 5,667,477 A | 9/1997 | Segawa |
| 5,674,182 A | 10/1997 | Suzuki et al. |
| 5,674,197 A | 10/1997 | van Muiden et al. |
| 5,685,823 A | 11/1997 | Ito et al. |
| 5,685,825 A | 11/1997 | Takase et al. |
| 5,691,853 A | 11/1997 | Miyano |
| 5,695,450 A | 12/1997 | Yabe et al. |
| 5,698,866 A | 12/1997 | Doiron et al. |
| 5,702,349 A | 12/1997 | Morizumi |
| 5,703,724 A | 12/1997 | Miyano |
| 5,704,371 A | 1/1998 | Shepard |
| 5,704,896 A | 1/1998 | Fukunishi et al. |
| 5,708,482 A | 1/1998 | Takahashi et al. |
| 5,721,566 A | 2/1998 | Rosenberg et al. |
| 5,724,068 A | 3/1998 | Sanchez et al. |
| 5,728,045 A | 3/1998 | Komi |
| 5,738,106 A * | 4/1998 | Yamamori et al. ............ 600/532 |
| 5,739,811 A | 4/1998 | Rosenberg et al. |
| 5,740,801 A | 4/1998 | Branson |
| 5,746,696 A | 5/1998 | Kondo |
| 5,764,809 A | 6/1998 | Nomami et al. |
| 5,767,839 A | 6/1998 | Rosenberg |
| 5,781,172 A | 7/1998 | Engel et al. |
| 5,788,714 A | 8/1998 | Ouchi |
| 5,789,047 A | 8/1998 | Sasaki et al. |
| 5,793,539 A | 8/1998 | Konno et al. |
| 5,805,140 A | 9/1998 | Rosenberg et al. |
| 5,810,715 A | 9/1998 | Moriyama |
| 5,812,983 A | 9/1998 | Kumagai |
| 5,819,736 A | 10/1998 | Avny et al. |
| 5,820,591 A | 10/1998 | Thompson et al. |
| 5,821,466 A | 10/1998 | Clark et al. |
| 5,821,920 A | 10/1998 | Rosenberg et al. |
| 5,823,948 A | 10/1998 | Ross, Jr. et al. |
| 5,827,186 A | 10/1998 | Chen et al. |
| 5,827,190 A | 10/1998 | Palcic et al. |
| 5,828,197 A | 10/1998 | Martin et al. |
| 5,828,363 A | 10/1998 | Yaniger et al. |
| 5,830,124 A | 11/1998 | Suzuki et al. |
| 5,830,128 A | 11/1998 | Tanaka |
| 5,836,869 A | 11/1998 | Kudo et al. |
| 5,837,023 A | 11/1998 | Koike et al. |
| 5,840,014 A | 11/1998 | Miyano et al. |
| 5,841,126 A | 11/1998 | Fossum et al. |
| 5,843,000 A | 12/1998 | Nishioka et al. |
| 5,846,183 A | 12/1998 | Chilcoat |
| 5,855,560 A | 1/1999 | Idaomi et al. |
| 5,857,963 A | 1/1999 | Pelchy et al. |
| 5,865,724 A | 2/1999 | Palmer et al. |
| 5,868,664 A | 2/1999 | Speier et al. |
| 5,868,666 A | 2/1999 | Okada et al. |
| 5,873,816 A | 2/1999 | Kagawa et al. |
| 5,873,866 A | 2/1999 | Kondo et al. |
| 5,876,326 A | 3/1999 | Takamura et al. |
| 5,876,331 A | 3/1999 | Wu et al. |
| 5,876,373 A | 3/1999 | Giba et al. |
| 5,876,427 A | 3/1999 | Chen et al. |
| 5,877,819 A | 3/1999 | Branson |
| 5,879,284 A | 3/1999 | Tsujita |
| 5,880,714 A | 3/1999 | Rosenberg et al. |
| 5,882,293 A | 3/1999 | Ouchi |
| 5,882,339 A | 3/1999 | Beiser et al. |
| 5,889,670 A | 3/1999 | Schuler et al. |
| 5,889,672 A | 3/1999 | Schuler et al. |
| 5,892,630 A | 4/1999 | Broome |
| 5,895,350 A | 4/1999 | Hori |
| 5,897,507 A | 4/1999 | Kortenbach et al. |
| 5,897,525 A | 4/1999 | Dey et al. |
| 5,907,487 A | 5/1999 | Rosenberg et al. |
| 5,923,018 A | 7/1999 | Kameda et al. |
| 5,928,136 A | 7/1999 | Barry |
| 5,929,607 A | 7/1999 | Rosenberg et al. |
| 5,929,846 A | 7/1999 | Rosenberg et al. |
| 5,929,900 A | 7/1999 | Yamanaka |
| 5,929,901 A | 7/1999 | Adair et al. |
| 5,931,833 A | 8/1999 | Silverstein |
| 5,933,809 A | 8/1999 | Hunt et al. |
| 5,935,085 A | 8/1999 | Welsh et al. |
| 5,936,778 A | 8/1999 | Miyano et al. |
| 5,941,817 A | 8/1999 | Crawford |
| 5,950,168 A | 9/1999 | Simborg et al. |
| 5,951,462 A | 9/1999 | Yamanaka |
| 5,956,416 A | 9/1999 | Tsuruoka et al. |
| 5,956,689 A | 9/1999 | Everhart |
| 5,956,690 A | 9/1999 | Haggerson et al. |
| 5,959,613 A | 9/1999 | Rosenberg et al. |
| 5,976,070 A | 11/1999 | Ono et al. |
| 5,976,074 A | 11/1999 | Moriyama |
| 5,980,454 A | 11/1999 | Broome |
| 5,980,468 A | 11/1999 | Zimmon |
| 5,986,693 A | 11/1999 | Adair et al. |
| 5,991,729 A | 11/1999 | Barry et al. |
| 5,991,730 A | 11/1999 | Lubin et al. |
| 5,999,168 A | 12/1999 | Rosenberg et al. |
| 6,002,425 A | 12/1999 | Yamanaka et al. |
| 6,007,531 A | 12/1999 | Snoke et al. |
| 6,014,630 A | 1/2000 | Jeacock et al. |
| 6,015,088 A | 1/2000 | Parker et al. |
| 6,017,322 A | 1/2000 | Snoke et al. |
| 6,020,875 A | 2/2000 | Moore et al. |
| 6,020,876 A | 2/2000 | Rosenberg et al. |
| 6,026,363 A | 2/2000 | Shepard |
| 6,030,360 A | 2/2000 | Biggs |
| 6,032,120 A | 2/2000 | Rock et al. |
| 6,039,728 A | 3/2000 | Berlien et al. |
| 6,043,839 A | 3/2000 | Adair et al. |
| 6,050,718 A | 4/2000 | Schena et al. |
| 6,057,828 A | 5/2000 | Rosenberg et al. |
| 6,059,719 A | 5/2000 | Yamamoto et al. |

| | | | | | | |
|---|---|---|---|---|---|---|
| 6,061,004 | A | 5/2000 | Rosenberg | 6,540,669 | B2 | 4/2003 | Abe et al. |
| 6,067,077 | A | 5/2000 | Martin et al. | 6,544,194 | B1 | 4/2003 | Kortenbach et al. |
| 6,071,248 | A | 6/2000 | Zimmon | 6,545,703 | B1 | 4/2003 | Takahashi et al. |
| 6,075,555 | A | 6/2000 | Street | 6,551,239 | B2 | 4/2003 | Renner et al. |
| 6,078,308 | A | 6/2000 | Rosenberg et al. | 6,558,317 | B2 | 5/2003 | Takahashi et al. |
| 6,078,353 | A | 6/2000 | Yamanaka et al. | 6,561,971 | B1 | 5/2003 | Akiba |
| 6,078,876 | A | 6/2000 | Rosenberg et al. | 6,565,507 | B2 | 5/2003 | Kamata et al. |
| 6,080,104 | A | 6/2000 | Ozawa et al. | 6,574,629 | B1 | 6/2003 | Cooke, Jr. et al. |
| 6,081,809 | A | 6/2000 | Kumagai | 6,589,162 | B2 | 7/2003 | Nakashima et al. |
| 6,083,152 | A | 7/2000 | Strong | 6,595,913 | B2 | 7/2003 | Takahashi |
| 6,083,170 | A | 7/2000 | Ben-Haim | 6,597,390 | B1 | 7/2003 | Higuchi |
| 6,095,971 | A | 8/2000 | Takahashi | 6,599,239 | B2 | 7/2003 | Hayakawa et al. |
| 6,099,465 | A | 8/2000 | Inoue | 6,599,252 | B2 * | 7/2003 | Starr ........................... 600/532 |
| 6,100,874 | A | 8/2000 | Schena et al. | 6,602,186 | B1 | 8/2003 | Sugimoto et al. |
| 6,104,382 | A | 8/2000 | Martin et al. | 6,605,035 | B2 | 8/2003 | Ando et al. |
| 6,120,435 | A | 9/2000 | Eino | 6,609,135 | B1 | 8/2003 | Omori et al. |
| 6,125,337 | A | 9/2000 | Rosenberg et al. | 6,611,846 | B1 | 8/2003 | Stoodley |
| 6,128,006 | A | 10/2000 | Rosenberg et al. | 6,614,969 | B2 | 9/2003 | Eichelberger et al. |
| 6,132,369 | A | 10/2000 | Takahashi | 6,616,601 | B2 | 9/2003 | Hayakawa |
| 6,134,056 | A | 10/2000 | Nakamura | 6,623,424 | B2 | 9/2003 | Hayakawa et al. |
| 6,134,506 | A | 10/2000 | Rosenberg et al. | 6,638,214 | B2 | 10/2003 | Akiba |
| 6,135,946 | A | 10/2000 | Konen et al. | 6,638,215 | B2 | 10/2003 | Kobayashi |
| 6,139,508 | A | 10/2000 | Simpson et al. | 6,641,528 | B2 | 11/2003 | Torii |
| 6,141,037 | A | 10/2000 | Upton et al. | 6,651,669 | B1 | 11/2003 | Burnside |
| 6,142,956 | A | 11/2000 | Kortenbach et al. | 6,656,110 | B1 | 12/2003 | Irion et al. |
| 6,146,355 | A | 11/2000 | Biggs | 6,656,112 | B2 | 12/2003 | Miyanaga |
| 6,149,607 | A | 11/2000 | Simpson et al. | 6,656,127 | B1 | 12/2003 | Ben-Oren et al. |
| 6,152,877 | A | 11/2000 | Masters | 6,659,940 | B2 | 12/2003 | Adler |
| 6,154,198 | A | 11/2000 | Rosenberg | 6,663,561 | B2 | 12/2003 | Sugimoto et al. |
| 6,154,248 | A | 11/2000 | Ozawa et al. | 6,669,629 | B2 | 12/2003 | Matsui |
| 6,155,988 | A | 12/2000 | Peters | 6,673,012 | B2 | 1/2004 | Fujii et al. |
| 6,181,481 | B1 | 1/2001 | Yamamoto et al. | 6,677,984 | B2 | 1/2004 | Kobayashi et al. |
| 6,184,922 | B1 | 2/2001 | Saito et al. | 6,678,397 | B1 | 1/2004 | Omori et al. |
| 6,193,714 | B1 | 2/2001 | McGaffigan et al. | 6,682,479 | B1 | 1/2004 | Takahashi et al. |
| 6,195,592 | B1 | 2/2001 | Schuler et al. | 6,685,631 | B2 | 2/2004 | Minami |
| 6,203,493 | B1 | 3/2001 | Ben-Haim | 6,686,949 | B2 | 2/2004 | Kobayashi et al. |
| 6,206,824 | B1 | 3/2001 | Ohara et al. | 6,690,409 | B1 | 2/2004 | Takahashi |
| 6,211,904 | B1 | 4/2001 | Adair | 6,690,963 | B2 | 2/2004 | Ben-Haim et al. |
| 6,216,104 | B1 | 4/2001 | Moshfeghi et al. | 6,692,431 | B2 | 2/2004 | Kazakevich |
| 6,219,091 | B1 | 4/2001 | Yamanaka et al. | 6,697,101 | B1 | 2/2004 | Takahashi et al. |
| 6,221,070 | B1 | 4/2001 | Tu et al. | 6,699,181 | B2 | 3/2004 | Wako |
| 6,241,668 | B1 | 6/2001 | Herzog | 6,702,737 | B2 | 3/2004 | Hinto et al. |
| 6,260,994 | B1 | 7/2001 | Matsumoto et al. | 6,711,426 | B2 | 3/2004 | Benaron et al. |
| 6,272,470 | B1 | 8/2001 | Teshima | 6,715,068 | B1 | 3/2004 | Abe |
| 6,275,255 | B1 | 8/2001 | Adair et al. | 6,716,162 | B2 | 4/2004 | Hakamata |
| 6,283,960 | B1 | 9/2001 | Ashley | 6,728,599 | B2 | 4/2004 | Wang et al. |
| 6,295,082 | B1 | 9/2001 | Dowdy et al. | 6,730,018 | B2 | 5/2004 | Takase |
| 6,299,625 | B1 | 10/2001 | Bacher | 6,736,773 | B2 | 5/2004 | Wendlandt et al. |
| 6,309,347 | B1 | 10/2001 | Takahashi et al. | 6,743,240 | B2 | 6/2004 | Smith et al. |
| 6,310,642 | B1 | 10/2001 | Adair et al. | 6,749,559 | B1 | 6/2004 | Krass et al. |
| 6,319,196 | B1 | 11/2001 | Minami | 6,749,560 | B1 | 6/2004 | Konstorum et al. |
| 6,319,197 | B1 | 11/2001 | Tsuji et al. | 6,749,561 | B2 | 6/2004 | Kazakevich |
| 6,334,844 | B1 | 1/2002 | Akiba | 6,753,905 | B1 | 6/2004 | Okada et al. |
| 6,346,075 | B1 | 2/2002 | Arai et al. | 6,758,806 | B2 | 7/2004 | Kamrava et al. |
| 6,366,799 | B1 | 4/2002 | Acker et al. | 6,758,807 | B2 | 7/2004 | Minami |
| 6,381,029 | B1 | 4/2002 | Tipirneni | 6,758,842 | B2 | 7/2004 | Irion et al. |
| 6,398,724 | B1 | 6/2002 | May et al. | 6,778,208 | B1 | 8/2004 | Takeshige et al. |
| 6,413,207 | B1 | 7/2002 | Minami | 6,780,151 | B2 | 8/2004 | Grabover et al. |
| 6,421,078 | B1 | 7/2002 | Akai et al. | 6,785,410 | B2 | 8/2004 | Vining et al. |
| 6,425,535 | B1 | 7/2002 | Akiba | 6,785,593 | B2 | 8/2004 | Wang et al. |
| 6,425,858 | B1 | 7/2002 | Minami | 6,796,938 | B2 | 9/2004 | Sendai |
| 6,436,032 | B1 | 8/2002 | Eto et al. | 6,796,939 | B1 | 9/2004 | Hirata et al. |
| 6,441,845 | B1 | 8/2002 | Matsumoto | 6,798,533 | B2 | 9/2004 | Tipirneni |
| 6,447,444 | B1 | 9/2002 | Avni et al. | 6,800,056 | B2 | 10/2004 | Tartaglia et al. |
| 6,449,006 | B1 | 9/2002 | Shipp | 6,800,057 | B2 | 10/2004 | Tsujita et al. |
| 6,453,190 | B1 | 9/2002 | Acker et al. | 6,808,491 | B2 | 10/2004 | Kortenbach et al. |
| 6,454,162 | B1 | 9/2002 | Teller | 6,824,539 | B2 | 11/2004 | Novak |
| 6,459,447 | B1 | 10/2002 | Okada et al. | 6,824,548 | B2 | 11/2004 | Smith et al. |
| 6,468,204 | B2 | 10/2002 | Sendai et al. | 6,829,003 | B2 | 12/2004 | Takami |
| 6,475,141 | B2 | 11/2002 | Abe | 6,830,545 | B2 | 12/2004 | Bendall |
| 6,478,730 | B1 | 11/2002 | Bala et al. | 6,832,990 | B2 | 12/2004 | Kortenbach et al. |
| 6,489,987 | B1 | 12/2002 | Higuchi et al. | 6,840,932 | B2 | 1/2005 | Lang et al. |
| 6,496,827 | B2 | 12/2002 | Kozam et al. | 6,842,196 | B1 | 1/2005 | Swift et al. |
| 6,498,948 | B1 | 12/2002 | Ozawa et al. | 6,846,286 | B2 | 1/2005 | Suzuki et al. |
| 6,503,193 | B1 | 1/2003 | Iwasaki et al. | 6,847,933 | B1 | 1/2005 | Hastings |
| 6,520,908 | B1 | 2/2003 | Ikeda et al. | 6,849,043 | B2 | 2/2005 | Kondo |
| 6,524,234 | B2 | 2/2003 | Ouchi | 6,850,794 | B2 | 2/2005 | Shahidi |
| 6,530,882 | B1 | 3/2003 | Farkas et al. | 6,855,109 | B2 | 2/2005 | Obata et al. |
| 6,533,722 | B2 | 3/2003 | Nakashima | 6,858,004 | B1 | 2/2005 | Ozawa et al. |

| | | |
|---|---|---|
| 6,858,014 B2 | 2/2005 | Damarati |
| 6,860,849 B2 | 3/2005 | Matsushita et al. |
| 6,863,650 B1 | 3/2005 | Irion |
| 6,863,661 B2 | 3/2005 | Carrillo et al. |
| 6,868,195 B2 | 3/2005 | Fujita |
| 6,871,086 B2 | 3/2005 | Nevo et al. |
| 6,873,352 B2 | 3/2005 | Mochida et al. |
| 6,876,380 B2 | 4/2005 | Abe et al. |
| 6,879,339 B2 | 4/2005 | Ozawa |
| 6,881,188 B2 | 4/2005 | Furuya et al. |
| 6,882,785 B2 | 4/2005 | Eichelberger et al. |
| 6,887,195 B1 | 5/2005 | Pilvisto |
| 6,890,294 B2 | 5/2005 | Niwa et al. |
| 6,892,090 B2 | 5/2005 | Verard et al. |
| 6,892,112 B2 | 5/2005 | Wang et al. |
| 6,895,268 B1 | 5/2005 | Rahn et al. |
| 6,898,086 B2 | 5/2005 | Takami et al. |
| 6,899,673 B2 | 5/2005 | Ogura et al. |
| 6,899,674 B2 | 5/2005 | Viebach et al. |
| 6,899,705 B2 | 5/2005 | Niemeyer |
| 6,900,829 B1 | 5/2005 | Ozawa et al. |
| 6,902,527 B1 | 6/2005 | Doguchi et al. |
| 6,902,529 B2 | 6/2005 | Onishi et al. |
| 6,903,761 B1 | 6/2005 | Abe et al. |
| 6,903,883 B2 | 6/2005 | Amanai |
| 6,905,057 B2 | 6/2005 | Swayze et al. |
| 6,905,462 B1 | 6/2005 | Homma |
| 6,908,427 B2 | 6/2005 | Fleener et al. |
| 6,908,429 B2 | 6/2005 | Heimberger et al. |
| 6,911,916 B1 | 6/2005 | Wang et al. |
| 6,916,286 B2 | 7/2005 | Kazakevich |
| 6,921,369 B1 * | 7/2005 | Gehrke et al. ............... 600/529 |
| 6,923,818 B2 | 8/2005 | Muramatsu et al. |
| 6,928,490 B1 | 8/2005 | Bucholz et al. |
| 6,930,706 B2 | 8/2005 | Kobayashi et al. |
| 6,932,761 B2 | 8/2005 | Maeda et al. |
| 6,934,093 B2 | 8/2005 | Kislev et al. |
| 6,934,575 B2 | 8/2005 | Ferre et al. |
| 6,943,663 B2 | 9/2005 | Wang et al. |
| 6,943,946 B2 | 9/2005 | Fiete |
| 6,943,959 B2 | 9/2005 | Homma |
| 6,943,966 B2 | 9/2005 | Konno |
| 6,944,031 B2 | 9/2005 | Takami et al. |
| 6,949,068 B2 | 9/2005 | Taniguchi et al. |
| 6,950,691 B2 | 9/2005 | Uchikubo |
| 6,955,671 B2 | 10/2005 | Uchikubo |
| 7,036,504 B2 * | 5/2006 | Wallace et al. .......... 128/202.22 |
| 7,565,907 B2 * | 7/2009 | Curti et al. ............... 128/207.18 |
| 7,578,793 B2 * | 8/2009 | Todros et al. ............... 600/484 |
| 2001/0039370 A1 | 11/2001 | Takahashi et al. |
| 2001/0049491 A1 | 12/2001 | Shimada |
| 2002/0017515 A1 | 2/2002 | Obata et al. |
| 2002/0028984 A1 | 3/2002 | Hayakawa et al. |
| 2002/0055669 A1 | 5/2002 | Konno |
| 2002/0080248 A1 | 6/2002 | Adair et al. |
| 2002/0087048 A1 | 7/2002 | Brock et al. |
| 2002/0087166 A1 | 7/2002 | Brock et al. |
| 2002/0095175 A1 | 7/2002 | Brock et al. |
| 2002/0128633 A1 | 9/2002 | Brock et al. |
| 2002/0193664 A1 | 12/2002 | Ross et al. |
| 2003/0032863 A1 | 2/2003 | Kazakevich |
| 2003/0051733 A1 | 3/2003 | Kotmel |
| 2003/0069897 A1 | 4/2003 | Roy et al. |
| 2003/0106553 A1 | 6/2003 | Vanderveen |
| 2003/0149338 A1 | 8/2003 | Francois et al. |
| 2003/0181905 A1 | 9/2003 | Long |
| 2003/0214409 A1 | 11/2003 | Hickle |
| 2004/0030367 A1 | 2/2004 | Yamaki |
| 2004/0049097 A1 | 3/2004 | Miyake |
| 2004/0054258 A1 | 3/2004 | Maeda et al. |
| 2004/0073083 A1 | 4/2004 | Ikeda et al. |
| 2004/0073084 A1 | 4/2004 | Maeda et al. |
| 2004/0073085 A1 | 4/2004 | Ikeda et al. |
| 2004/0097805 A1 * | 5/2004 | Verard et al. ............... 600/428 |
| 2004/0147809 A1 | 7/2004 | Kazakevich |
| 2004/0167379 A1 | 8/2004 | Akiba |
| 2004/0249247 A1 | 12/2004 | Iddan |
| 2004/0257608 A1 | 12/2004 | Tipirneni |
| 2005/0065447 A1 * | 3/2005 | Lee et al. ............... 600/529 |
| 2005/0177096 A1 * | 8/2005 | Bollish et al. ............... 604/65 |
| 2005/0197861 A1 | 9/2005 | Omori et al. |
| 2005/0203341 A1 | 9/2005 | Welker et al. |
| 2005/0228697 A1 | 10/2005 | Funahashi |

FOREIGN PATENT DOCUMENTS

| | | |
|---|---|---|
| EP | 0 512 535 B1 | 8/1997 |
| EP | 1 300 883 A2 | 4/2003 |
| JP | 58-78635 A | 5/1983 |
| JP | 05-31071 A | 2/1993 |
| JP | 05-091972 A | 4/1993 |
| JP | 06-105800 A | 4/1994 |
| JP | 06-254048 A | 9/1994 |
| JP | 07-8441 A | 1/1995 |
| JP | 10-113330 A | 5/1998 |
| JP | 10-286221 A | 10/1998 |
| JP | 11-216113 A | 8/1999 |
| JP | 3219521 B2 | 8/2001 |
| JP | 2002-102152 A2 | 4/2002 |
| JP | 2002-177197 A2 | 6/2002 |
| JP | 2002-185873 A2 | 6/2002 |
| JP | 2002-253481 A2 | 9/2002 |
| JP | 3372273 B2 | 11/2002 |
| JP | 2002345781 A | 12/2002 |
| JP | 2003-75113 A2 | 3/2003 |
| JP | 3482238 B2 | 10/2003 |
| WO | WO 93/13704 A1 | 7/1993 |
| WO | WO 00/74631 A2 | 12/2000 |
| WO | WO 2004/016310 A2 | 2/2004 |
| WO | WO 2005/023082 A2 | 3/2005 |

OTHER PUBLICATIONS

Nadkarni, U.B., et al., "Non-Invasive Respiratory Monitoring in Paediatric Intensive Care Unit," *J. Postgrad. Med.* 46(2):149-152, 2000.

"Physics and Anesthesiology," www.pharmacology200.com, n.d., <http://www.pharmacology2000.com/physics/Chemistry_Physics/physics12.htm>[retrieved Jun. 17, 2004].

* cited by examiner

ENDOSCOPIC SYSTEM WITH INTEGRATED PATIENT RESPIRATORY STATUS INDICATOR

FIELD OF THE INVENTION

The present invention relates to an endoscopic system, and in particular, to an endoscopic system having integrated patient respiratory status monitoring capabilities.

BACKGROUND OF THE INVENTION

Endoscopes have been used for many years in the medical field to look within a selected region of a patient's body, e.g., the colon or the upper gastrointestinal region. The endoscope is typically inserted through an orifice or a surgical incision into a body channel or cavity. Endoscopes are commonly used to perform surgical, therapeutic, diagnostic, or other medical procedures under direct visualization. Conventional endoscopes generally contain several endoscope components, such as fiber optic light guides, a fiber optic image guide, and a working channel. The endoscope can also be equipped with one or more instrument channels for surgical implements. These components are positioned within the lumen of an endoscope sheathing tube. Endoscopes may be rigid or flexible. Flexible endoscopes incorporate an elongated flexible shaft and may include an articulating distal tip to facilitate navigation through the internal curvature of a body cavity or channel. Examples of conventional endoscope designs are described in U.S. Pat. Nos. 4,706,656; 4,911,148; and 5,704,899.

In order to facilitate endoscopic procedures, patients often receive sedation. In recent years, fast acting sedation drugs, such as intravenous propofol, have been used in conjunction with endoscopic procedures. The use of sedation has required increased reliance on the use of monitoring devices to detect early signs of patient distress, such as heart rate, transcutaneous $PCO_2$, EKG and EEG for monitoring heart and brain functions, respectively, during surgery. The risk for patient respiratory distress, such as shock, is increased by any procedure that requires the use of a strong sedative, for example, in upper GI endoscopic procedures, such as endoscope retrograde cholangiopancreatography ("ERCP"), especially in frail patients.

While the conventional monitoring techniques work well for their intended use, they are not well suited for monitoring respiratory distress during various endoscopic procedures. One means of monitoring the respiratory status of a patient undergoing an endoscopic procedure is by measuring and charting the concentration of $CO_2$ in the patient's expired air, during the end-tidal phase ($ETCO_2$) of the respiratory cycle, in a procedure known as capnography. The capnographic unit is typically attached to a mask fitted over the patient's airway. However, a more sensitive means for measuring expired $CO_2$ is needed to provide early detection of patient respiratory distress during endoscopy.

SUMMARY OF THE INVENTION

To address the above-mentioned concerns and others, the present invention is an endoscopic system having an endoscopic probe routable through passageways of a surgical subject, the endoscopic probe having a proximal end and a distal end; and a capnographic sensor capable of generating signals indicative of $CO_2$ gas concentration during endoscopic use. In one embodiment, the capnographic sensor is positioned adjacent the distal end of the endoscopic probe. In another embodiment, the capnographic sensor is positioned between the proximal and distal end of the endoscopic probe. In yet another embodiment, the capnographic sensor is associated with a mouthpiece to be placed within the mouth or airway of the surgical subject. The capnographic sensor analyzes expired air from the subject, generates signals indicative of patient respiratory status, and outputs the generated signals to an output device, such as a control console, which synchronizes the $CO_2$ signals with the respiratory phase to determine the $ETCO_2$ of the patient

BRIEF DESCRIPTION OF THE DRAWINGS

The foregoing aspects and many of the attendant advantages of this invention will become more readily appreciated by reference to the following detailed description, when taken in conjunction with the accompanying drawings, wherein.

DETAILED DESCRIPTION OF EXEMPLARY EMBODIMENTS

Embodiments of the present invention will now be described with reference to the accompanying drawings where like numerals correspond to like elements. Embodiments of the present invention are directed to systems of the type broadly applicable to numerous medical applications in which it is desirable to insert a steerable or non-steerable imaging device, catheter or similar device into a body lumen or passageway. The following description provides examples of medical systems that include an endoscopic probe, a capnographic device, and a control console for use in medical procedures.

Several embodiments of the present invention include medical devices that incorporate endoscopic features, such as illumination and visualization capabilities, for endoscopically viewing anatomical structures within the body. As such, embodiments of the present invention can be used for a variety of different diagnostic and interventional procedures, including upper endoscopy, endoscope retrograde cholangiopancreatography ("ERCP"), bronchoscopy, thoracoscopy, colonoscopy, laparoscopy, ureteroscopy, hysteroscopy and video endoscopy, etc. The various embodiments of the present invention described herein may be used with both reusable and low cost, disposable endoscopes, such as an endoscope that is sufficiently inexpensive to manufacture such that it can be a single-use device as described in U.S. patent application Ser. No. 10/811,781, filed Mar. 29, 2004, and No. 10/956,007, filed Sep. 30, 2004, commonly assigned to Scimed Life Systems, Inc., now Boston Scientific Scimed, Inc.

Although exemplary embodiments of the present invention will be described hereinafter with reference to endoscopes, it will be appreciated that aspects of the present invention have wide application, and may be suitable for use with other medical devices, such as catheters (e.g., guide catheters, electrode catheters, etc.), and medical procedures where capnographic functionality may be desirable. Accordingly, the following descriptions and illustrations herein should be considered illustrative in nature, and thus, not limiting the scope of the present invention, as claimed.

Figure 1:
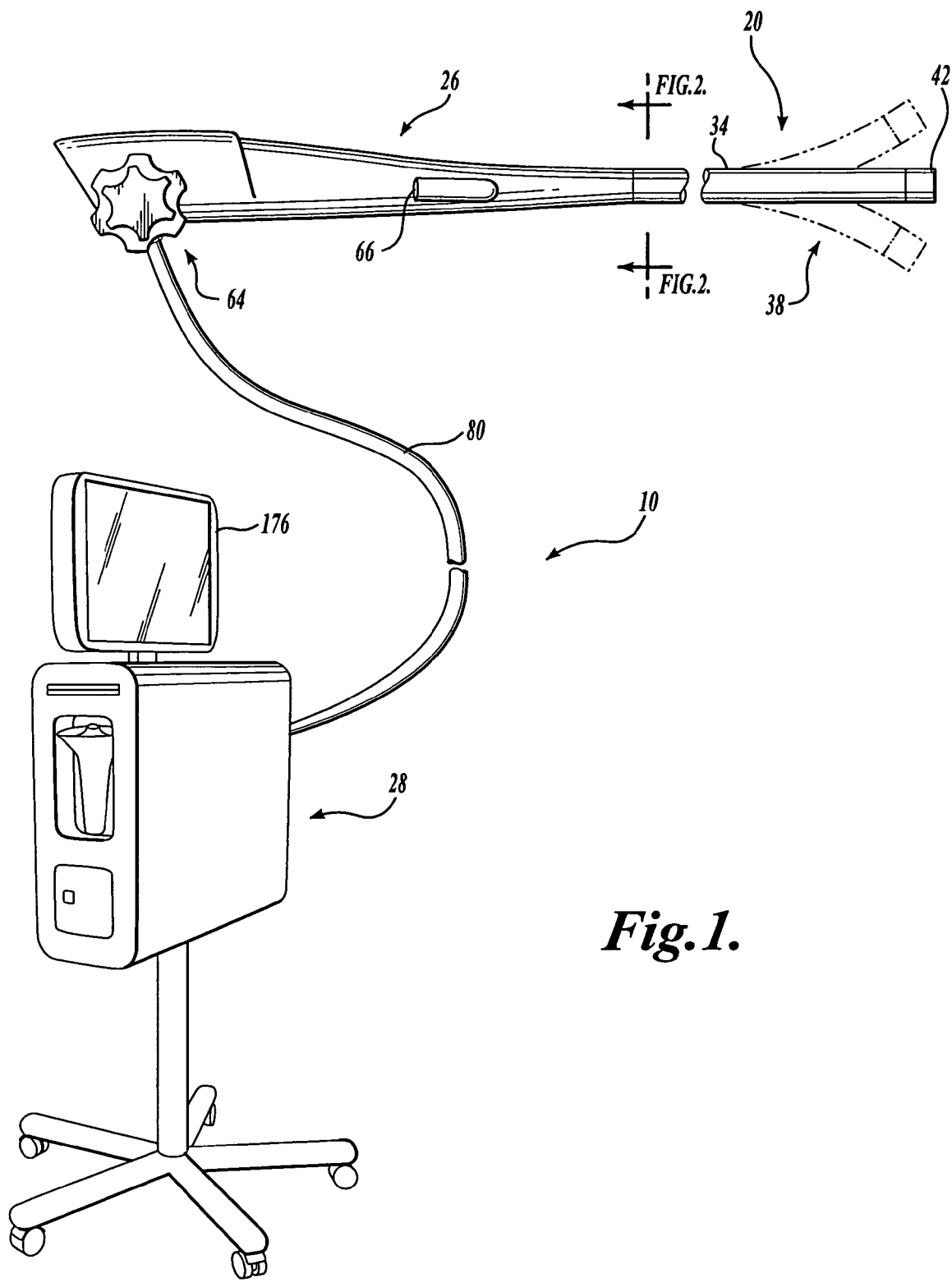
FIG. 1 is a perspective view of one embodiment of an endoscopic system formed in accordance with aspects of the present invention.
Figure 3:
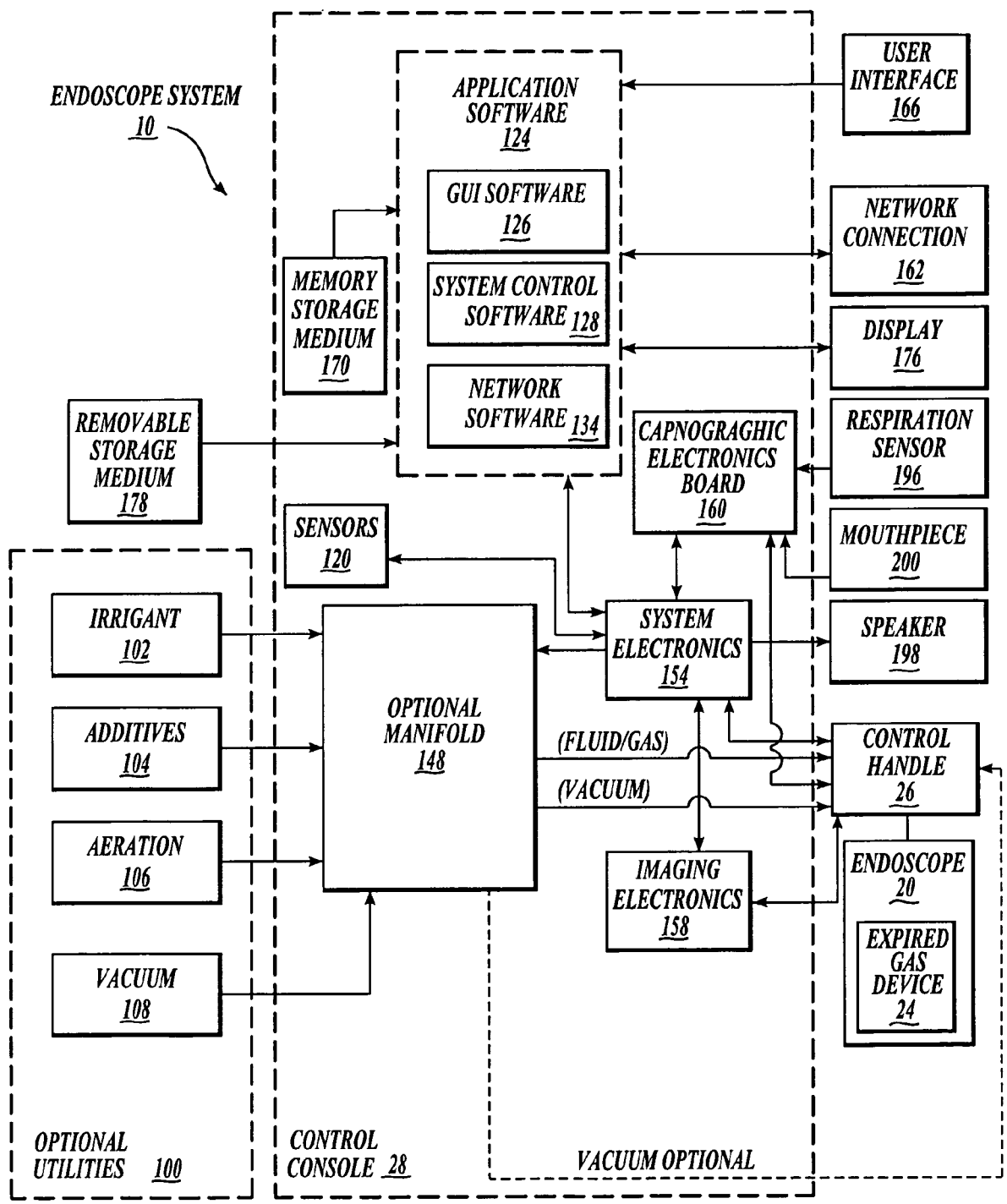
FIG. 3 is a functional block diagram of one embodiment of the endoscopic system of FIG. 1 formed in accordance with aspects of the present invention.

FIGS. 1 and 3 illustrate one embodiment of an exemplary endoscopic system, generally designated 10, formed in accordance with aspects of the present invention. The system 10 includes an endoscopic probe 20 and an expired air sampling device 24 (see FIG. 3) functionally connected to a control console 28. In one embodiment, the expired air sampling device 24 includes a capnographic sensor, as will be described in more detail below.

In use, the endoscopic probe 20 is routed through a body lumen of a patient to visualize a selected region of a patient's body. As the endoscopic probe 20 is routed through the body lumens, the expired air sampling device 24 collects expired air from the patient and generates signals indicative of patient respiratory status and outputs the generated signals to the control console 28. A patient respiration phase sensor 196 generates signals indicative of the phase of the patient's respiratory cycle. The respiration phase sensor 196 may be any type of sensor capable of detecting the respiration phase of the patient, such as, for example, a sensor such as a flow or pressure meter that measures the ventilated volume of gas or pressure from the patient, or a trans-thoracic impedance detector, or a strain gauge that measures chest movement. The control console 28, which includes system circuitry and application software, processes the signals received by the expired air sampling device 24 and the respiration phase sensor 196 in order to estimate the end-tidal $CO_2$ levels. The measured end-tidal $CO_2$ levels are monitored and compared to preset parameters in order to detect changes in the respiratory status of the patient. If the respiratory status of the patient changes based on the processed signals of the expired air sampling device 24, the control console 28 may output an audible or visual alert signal. Such alert signals may be useful to assure normal respiratory functioning of the patient under sedation.

Figure 2:
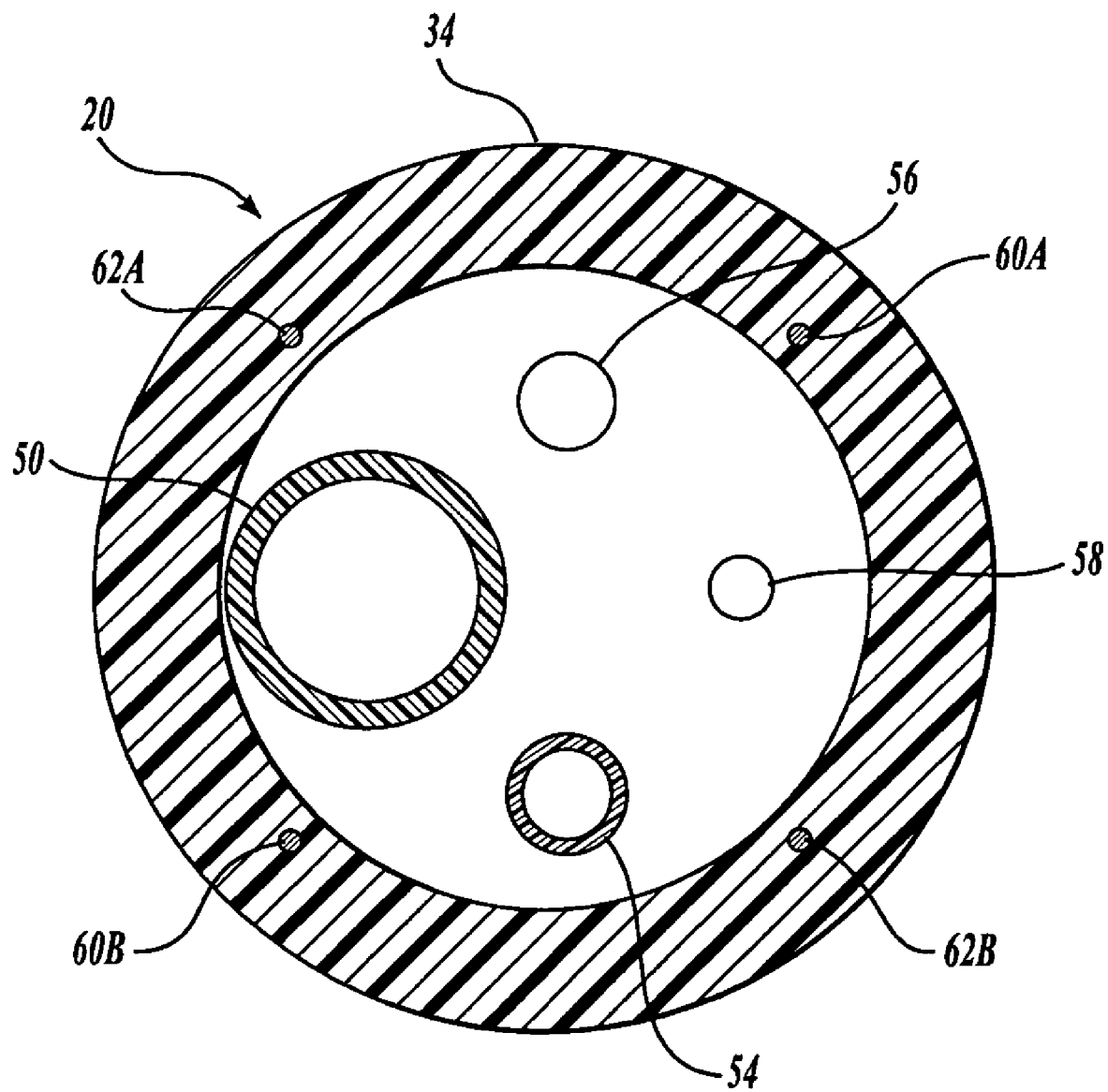
FIG. 2 is a cross sectional view of one embodiment of an insertion tube taken along the cross sectional line 2-2 in FIG. 1.

Referring now to FIGS. 1 and 2, the components of the system will be described in more detail. The endoscopic probe 20 can be any flexible, partially-flexible, or rigid elongated probe containing one or more lumens for the purpose of providing endoscopic procedures, and for the purpose of facilitating the insertion and extraction of fluids, gases, and/or medical devices into and out of the body. The endoscopic probe 20 may contain an imaging system of the optical type in which an optical image is carried on a coherent fiber optic bundle, or the video type, in which a miniature camera, which includes a charge coupled device (CCD) or CMOS imaging sensor, is disposed at the distal end of the endoscopic probe 20. In some embodiments, the endoscopic probe 20 is designed for a single-use and is disposable.

In one embodiment, the endoscopic probe 20 includes a flexible elongated insertion tube 34 having an articulation section 38 disposed at its distal region, and a distal tip 42. The distal tip 42 of the endoscopic probe 20 includes a digital imaging system (not shown) composed of, in one example, a CMOS image sensor, plastic optics, and LED illumination.

The endoscopic probe 20 further includes one or more lumens for the purpose of providing endoscopic procedures, and for the purpose of facilitating the insertion and extraction of fluids, gases, and/or medical devices into and out of the body. For example, the lumens may include a working channel 50, irrigation and/or insufflation lumen 54, and an optional suction lumen (not shown), as best shown in the cross sectional view of FIG. 2. In one embodiment, as will be described in detail below, the working channel 50 also functions as the suction lumen.

The endoscopic probe 20 also includes electrical cables 56 and 58 for supplying power to illumination LEDs and to transmit images back to the control console, respectively. Alternatively, fiber optic cables may be provided for sending and transmitting the same. Each lumen, fiber optic cable, an/or electrical cable extends from the distal tip of the endoscopic probe 20 to the control handle. Finally, in the embodiment shown, the endoscopic probe 20 includes at least one pair of control wires 60A-60B, and preferably, two pairs of control wires 60A-60B and 62A-62B, that are connected at the distal tip and terminate through the proximal end of the insertion tube 34.

Returning to FIG. 1, the proximal end of the insertion tube 34 enters the control handle 26, from which a communications conduit 80 emanates. The control handle 26 may include steering controls 64, such as one or more knobs, for selectively applying tension on the control wires to steer the distal tip 42 of the endoscopic probe. The control handle 26 may also include a biopsy port 66 for accessing of the lumens, such as the working channel, of the endoscopic probe. The communications conduit 80 functionally interconnects the control handle 26 to the control console 28. The communication conduit 80 carries image information back to imaging electronics housed in the control console 28 from, for example, the imaging sensor. Video related signals are exchanged between the control console 28 and the imaging sensor via electrical cable 58 passing through the insertion tube 34 and the communications conduit 80. As will be described in detail below, video data provided to the control console 28 by the imaging sensor may be placed in a suitable format for viewing and are transmitted to a display for viewing by the examining physician.

The communications conduit 80 also carries power for illumination LEDs forward from the control console 28 to the endoscopic probe 20, as well as optionally carrying irrigation/insufflation fluids forward through the insertion tube 34 to the distal tip of the endoscopic probe 20. In one embodiment, vacuum pressure is provided to the working channel through the communications connector 80. In one embodiment, the communications conduit 80 further carries expired gas ($CO_2$) concentration signals from the endoscopic probe to the control console 28. As will be described in detail below, expired gas signals provided to the control console 28 by the endoscopic probe may be processed in a suitable manner for viewing and are transmitted to a display for monitoring by an examining physician.

Each of the lumens as well as electrical cables that transmit control signals and, for example, expired gas concentration signals terminate at the proximal end of the communications conduit 80 in a communications terminal. The terminal is configured to be cooperatively connected to a control console terminal for establishing functional connection between the endoscopic probe 20 and the control console 28. As will be described in detail below, appropriate passageways, electrical cables, and the like interconnect the control console terminal to the respective components housed in the control console 28.

FIG. 3 is a block diagram of the system 10, including one exemplary embodiment of the control console 28. The control console 28 is preferably mounted on wheels so that it can easily be placed near a patient prior to an examination procedure. The control console 28 is connected to a source of electrical power, either AC mains or a battery, and optionally connected to a plurality of utilities 100, including, for example, an irrigant 102, a solution of additives 104, a supply of aeration 106, and a source of vacuum 108. The control console 28 further includes a suite of application software 124. The application software 124 includes a graphical user interface (GUI) software application 126, a system control software application 128, and a network software application 134. In addition, the control console 28 includes an optional manifold 148 for use with the utilities 100 for supplying fluids/gas to the endoscopic probe, a series of system electronics 154, an imaging electronics board 158, a capnographic electronics board 160, and a network connection 162. The network connection 162 may include, for example, a local area network or an Internet connection.

The suite of application software 124 resides on a computer readable memory storage medium 170, such as a hard disc drive, a solid state memory or other non-volatile memory, located in or associated with the control console 28, and may run on standard or custom operating systems and may be processed with processors used in personal computer environments. The GUI software application 126 is well known to those skilled in the art, and provides the physician or operator with live endoscopic video images and $CO_2$ concentration data, such as $ETCO_2$ values on display 176.

The system control software application 128 is the central control program of application software 124 that receives input from optional sensors 120, the user interface 166, the control handle 26, a respiration phase sensor 196, and the expired air sampling device 24 having a capnographic sensor via the system electronics 154, and provides system software control for a majority of features and functions necessary to operate and monitor the endoscopic system 10. Sensors 120 may include, for example, pressure transmitters and temperature sensors, and are used for real-time electronic feedback of hardware operating parameters such as pressure and temperature. The network software application 134 enables the operation of network connection 162 and is representative of the hardware and software required for local area network connection and connection to the World Wide Web.

The imaging electronics board 158 receives signals transmitted from an imaging sensor (not shown) and its associated electronics at the distal end of the endoscopic probe 20. Imaging electronics board 158 is electronically connected to system electronics 154. The application software 124 provides commands to the imaging electronics board 158 via the system electronics 154. The imaging electronics board 158 can enhance the images received or can provide video effects such as zoom, color changes, highlighting, etc., prior to display of the images on a display 176. The display 176 may be formed integrally with the control console or provided as an external monitor. Images produced by the imaging electronics board 158 may also be printed on a digital printer, sent to a network server to be, for example, archived, saved to a removable storage media 178, such as a floppy disc, CD, DVD, etc., or a video tape for later retrieval and analysis by a physician.

The imaging electronics board 158 also provides electrical power to a light source, such as a number of light emitting diodes (LEDs), at the distal end of the imaging endoscopic probe 20. Alternatively, if the endoscopic probe 20 utilizes an external light source, then the control console 28 can include a light intensity light source, such as a laser or arc lamp source, that supplies light to a fiber optic illumination guide within the imaging endoscopic probe 20 in order to illuminate an internal body organ. As will be described in detail below, the supply of power may be controlled by signals received from the control handle when the user desires to activate the light source or adjust the intensity of light produced. In one embodiment of the invention, the imaging board 158 is provided on a standard PC circuit board to allow individual endoscopes to be tested with a personal computer and without the need for an additional control console.

The capnographic electronics board 160 receives signals transmitted from the capnographic sensor of the expired air sampling device 24 that is located, in one example, at the distal end region of the endoscopic probe. The capnographic electronics board 160 is electronically connected to the system electronics 154. The application software 124 may provide commands to the capnographic electronics board 160 via the system electronics 154. The capnographic electronics board 160 may include A/D and D/A converters and other associated conventional components, such as preamplifiers, amplifiers, buffers, signal processors, comparators, conditioners, etc, in a conventional configuration for processing signals received from the capnographic sensor and an associated respiration phase sensor 196 and for outputting capnographic signals in a suitable format to be displayed as a capnogram on the display. The capnographic electronics board 160 contains software algorithms for estimating the $ETCO_2$ levels based on a correlation between the input signals from the expired air sampling device 24 and the input signal of the respiration phase sensor 196.

Figure 4:
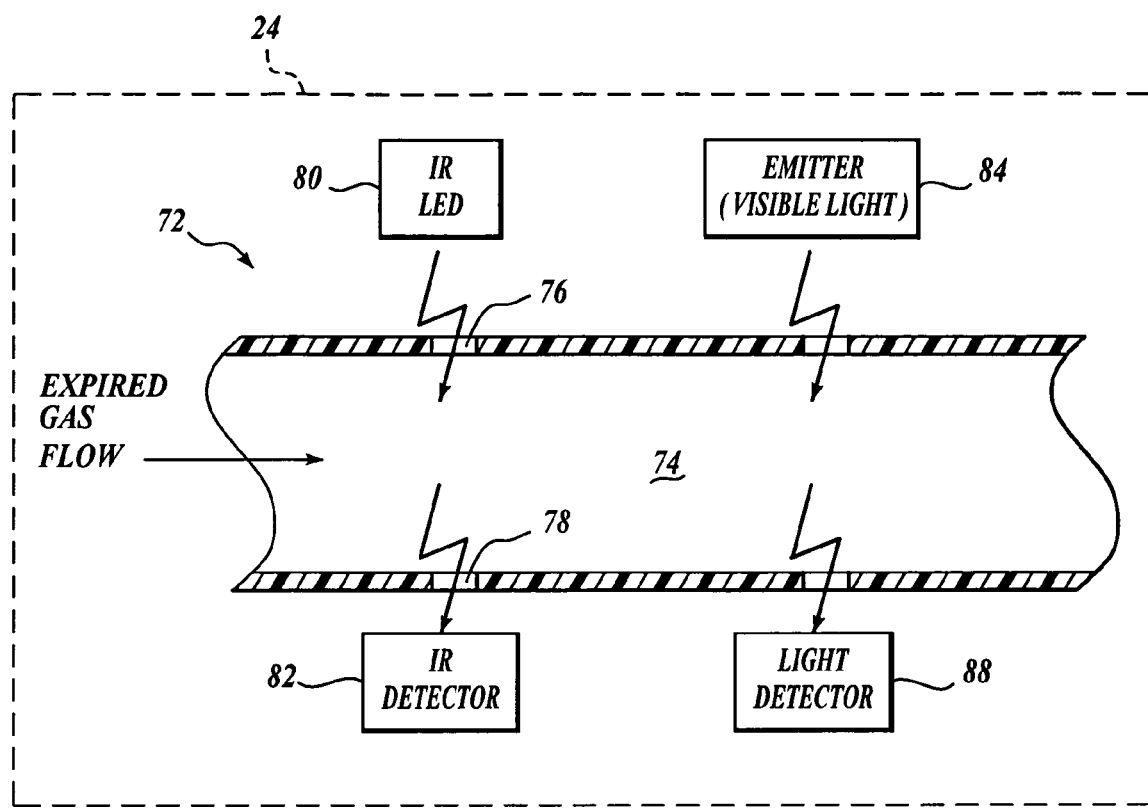
FIG. 4 is a schematic view of one embodiment of an exemplary expired air sampling device formed in accordance with aspects of the present invention for use with the endoscopic system of FIG. 1.

The system 10 also includes an expired air sampling device 24 functionally connected to the control console 28, as best shown in FIG. 3. The expired air sampling device 24 receives a quantity of expired air from the patient during the endoscopic medical procedure. Referring now to FIG. 4, there is shown one exemplary embodiment of the expired air sampling device 24. The expired air sampling device 24 includes a capnographic sensor 72 that analyzes the expired air in real-time for $CO_2$ content or concentration, and generates an electronic output signal corresponding to the instantaneous concentration levels of $CO_2$ present in the expired air. The expired air sampling device 24 preferably uses infrared spectroscopy analysis to generate the electronic output signals. However, other $CO_2$ analysis techniques, such as Raman or photoacoustic spectroscopy, may be practiced with the present invention. As will be explained in more detail below, the electronic output signals generated by the capnographic sensor 72 are transmitted to the control console 28, where the electronic output signals are processed by the capnographic electronics board 160 and displayed as a capnogram on the display 176.

In one embodiment shown schematically in FIG. 4, the capnographic sensor 72 may be configured as a cuvette that defines a sample chamber 74 through which expired air from the patient passes. A light port 76 and a detector port 78 are formed on opposite sides of the sample chamber 74. The light port 76 and the detector port 78 define an optical path of predetermined length across the sample chamber 74 for the optical detection of carbon dioxide flowing therethrough. An infrared light source 80 is provided and positioned such that infrared emitted by the infrared light source is transmitted through the light port 76 and along the optical path between the light port 76 and the detector port 78. Positioned at the end of the optical path through the detector port 78 is a photo detector 82. The photo detector 82 detects the infrared energy as it passes through the gas and the sample chamber 74, and generates electrical output signals representative thereof. As will be explained in more detail below, these output signals are processed for indicating the concentration of the one or more specific gases located in the sample chamber 74. The infrared light source may be of the specific frequency type, generating infrared by the high frequency-high voltage excitation of $CO_2$ at low pressure in a sealed tube, or may be a black body source filtered by an appropriate filter to provide infrared at the $CO_2$ wavelength in a range between 4.3 and 4.35 microns.

The capnographic sensor 72 may also include an optional reference cell that addresses gain and drift. As best shown in FIG. 4, the reference device includes a reference emitter 84, such as a visible light emitter, and a visible light detector 88 similarly arranged as the infrared light source and photo detector described above. Alternatively, the capnographic sensor 72 may include other electrical and/or mechanical techniques to address drift and/or calibration. For example, the sensing device may include the electrical chopper circuitry as described in U.S. Pat. No. 5,445,160, or the mechanical chopper wheel of U.S. Pat. No. 4,423,739, respectively, both of which are incorporated by reference. The reference cell provides a reference value to which the $CO_2$ concentration signals from the infrared detector may be compared by the capnographic electronics board 160.

Figure 5:
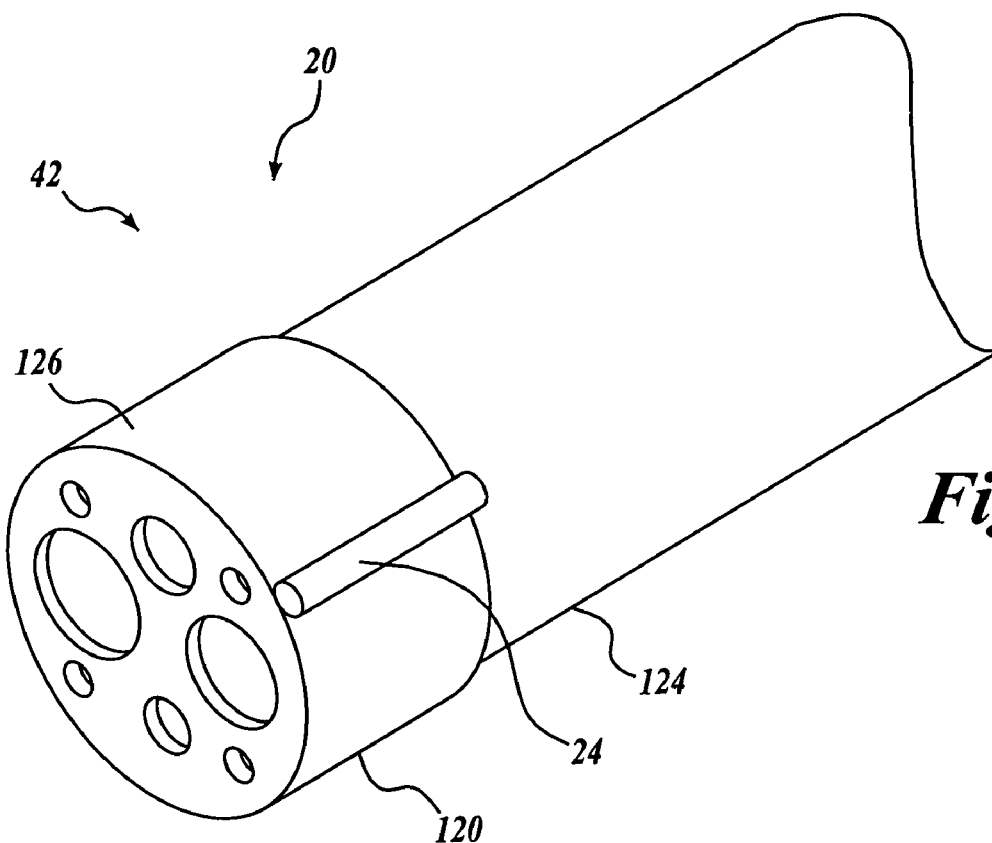
FIGS. 5-6 are perspective views of exemplary locations of the expired air sampling device in accordance with aspects of present invention.
Figure 6:
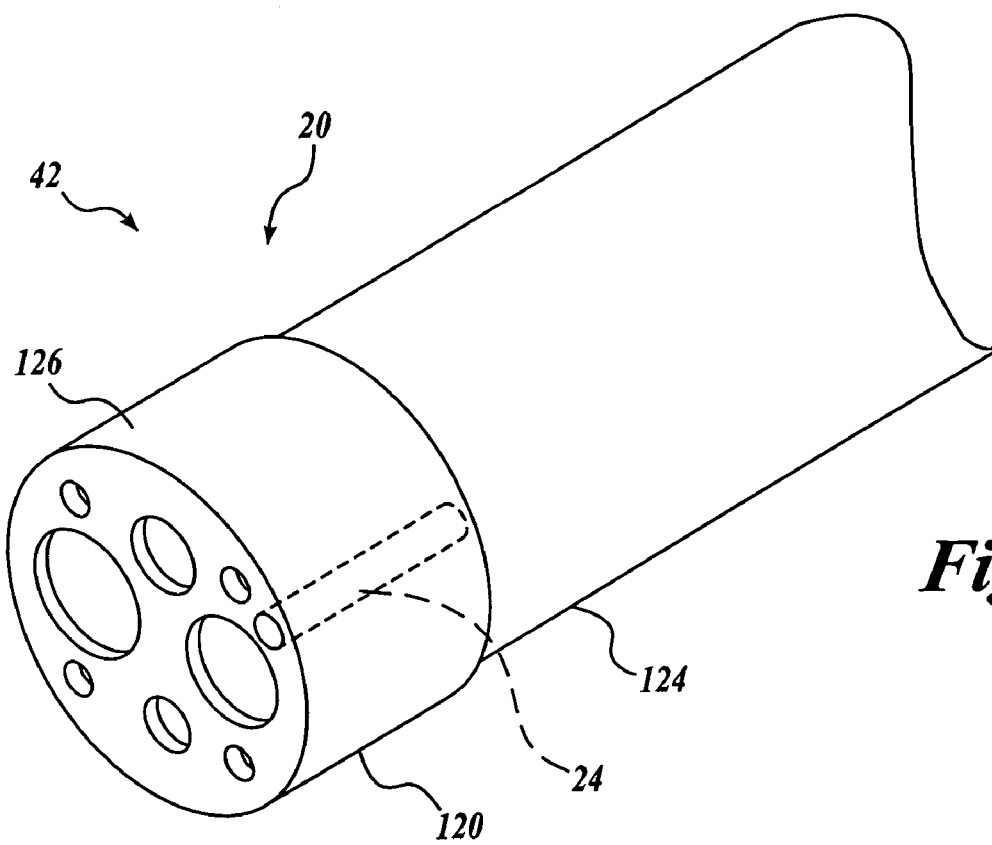

In several embodiments, the expired air sampling device 24 is attached to or integrated with the distal tip 42 of the endoscopic probe 20, as schematically shown in FIGS. 5 and 6, respectively. It will be appreciated that the expired air sampling device 24 may also be located along any portion of the probe shaft that is in communication with the airway of a patient when inserted. In another embodiment, the expired air sampling device 24 may be incorporated into a mouthpiece, as shown in FIG. 7.

Figure 7:
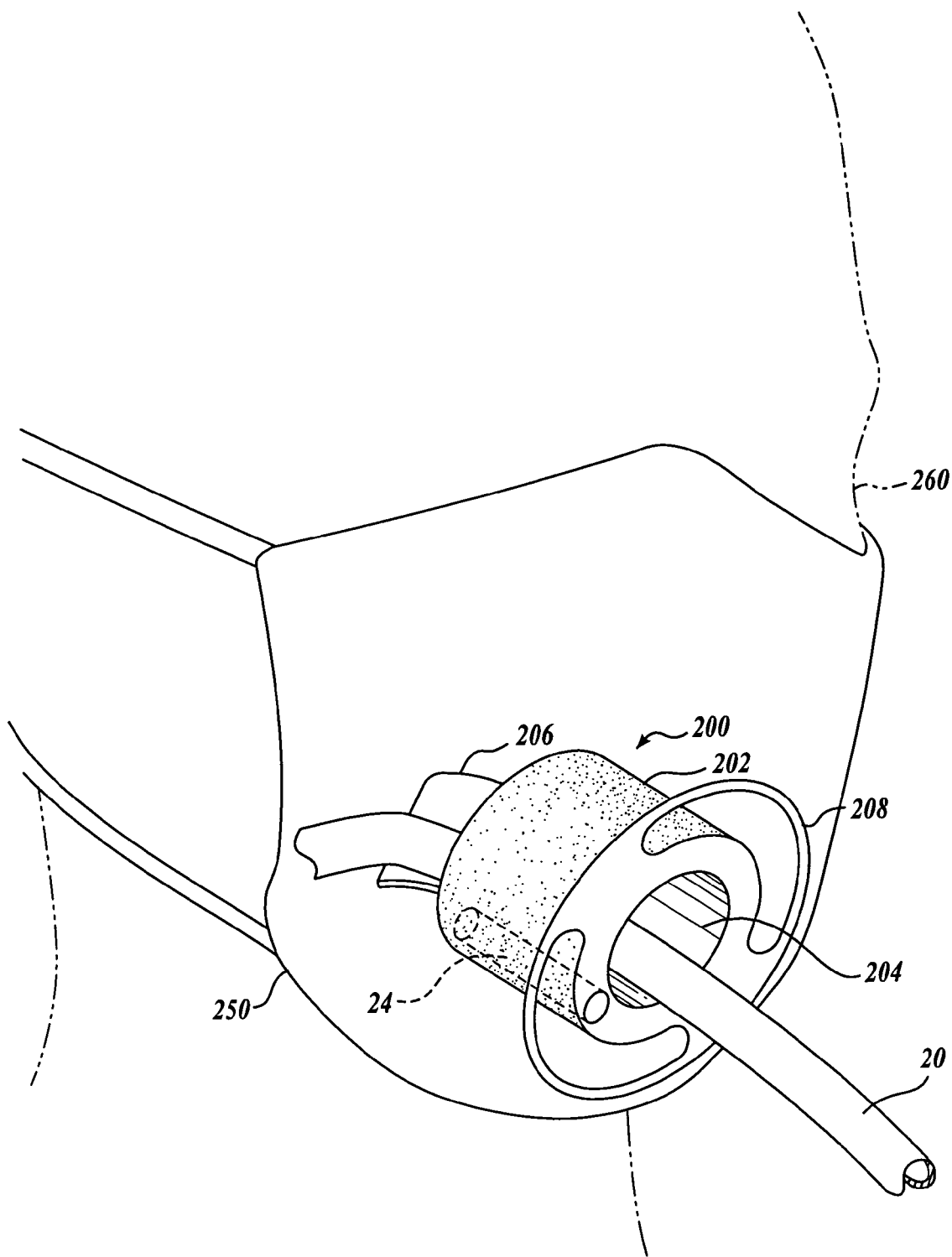
FIG. 7 is a perspective view of one embodiment of a mouthpiece and associated mask that incorporates the expired air sampling device of FIG. 4.

As best shown in FIG. 7, the mouthpiece 200 has a tube 202 that is positioned in the patient's mouth to provide access into the patient's alimentary or bronchial canals. The tube 202 defines a lumen 204 through which the endoscopic probe 20 may inserted for various medical procedures. The mouthpiece 200 may include a curved tongue 206 that extends distally from the tube 202 and operates to aid the passage of a catheter or endoscopic probe 20 into the patient's esophagus or trachea. In some embodiments, the outer surface of the tube 202 may be covered with a foam or other compressible material to protect the patient's teeth as surgical devices are inserted into the patient. Alternatively, the tube 202 itself may be formed of a relatively soft material. A flange 208 is positioned at the proximal end of the tube 202 and has a diameter larger than the patient's mouth such that the mouthpiece 200 cannot be accidentally swallowed by the patient. The mouthpiece 200 further includes inlet and outlet ports for communication with the sampling chamber of the expired air sampling device 24. The expired gas device is functionally connected to the control console via any suitable transmission means (not shown in FIG. 7). In the embodiment shown in FIG. 7, the mouthpiece 200 is associated with a surgical mask 250 that is fitted over the mouth and nose of a patient 260.

One suitable method of using the endoscopic system 10 will now be described with reference to FIGS. 1-7. In use, the endoscopic probe 20 is routed through a body lumen of a patient to visualize a selected region of a patient's body. Prior to, during, and/or subsequent the endoscopic probe 20 being routed through the body lumens, the expired air sampling device 24 collects expired air from the patient, generates signals indicative of patient respiratory status, such as $CO_2$ concentration levels, and outputs the generated signals to the control console 28. In one embodiment, the device 24 is located in a mouthpiece 200, which is positioned within the mouth region of the patient. In other embodiments, the device 24 is located along the proximal shaft of the insertion tube 34 or in proximity of the distal tip 42 of the endoscopic probe. It will be appreciated that the placement of the device 24 may be selected based on various factors, such as the type of medical procedure to be performed.

The control console 28, which includes appropriately configured circuitry, such as the systems electronics 154 and capnographic electronics board 160, and application software 124, receives the signals from the device 24 and the associated respiration phase sensor 196, such as a chest impedance sensor that outputs signals indicative of patient breath cycles, and processes the received signals. The control console 28 processes the signals by sampling the $CO_2$ concentration signals received by the device 24 in synchrony with the respiration phase determined by the respiration phase sensor 196. The processed signals are then outputted to the display as a capnogram, plotting, for example, $CO_2$ concentration versus time. Other data may be displayed on the display, such as $ETCO_2$ numerical values or $ETCO_2$ plotted over time to indicate any trends during the procedure.

The information displayed on the display 176 allows the physician to monitor the respiratory status of the patient. If the respiratory status of the patient changes based on the processed signals of the expired air sampling device 24 such that, for example, the breath by breath $ETCO_2$ values exceed a predetermined threshold, the control console 28 may output an audible signal through the speaker 198, or a visual alert signal on the display 176. Such alert signals may be useful to assure normal respiratory functioning of the patient under sedation and/or to alert the physician to early indications of respiratory distress in the patient.

In one embodiment of the present invention, the endoscopic probe 20, control handle 26, and communications conduit 80 (hereinafter "the single-use endoscope") may be used for single use application. Thus, upon completion of a patient examination procedure, the single use endoscope is disconnected from the control console 28 and disposed of. A new single-use endoscope is then connected to the control console 28 for the next examination procedure to be performed.

While exemplary embodiments of the present invention have been illustrated and described, it will be appreciated that various changes can be made therein without departing from the spirit and scope of the invention. It is therefore intended that the scope of the invention be determined from the following claims and equivalents thereof.

The embodiments of the invention in which an exclusive property or privilege is claimed are defined as follows:

1. An endoscope system, comprising:
   an endoscopic probe, the endoscopic probe having a proximal end, a distal end, and an elongate passageway extending between the proximal and distal ends; the elongate passageway configured to route at least one of an illumination system or a visualization system, wherein at least a distal end portion of the endoscopic probe is configured for insertion into a natural orifice of a body and routable through a tortuous natural lumen of the body; and
   a sampling device attached to the endoscopic probe at a position proximate the distal end portion of the endoscopic probe such that the sampling device is configured for insertion into the body, wherein the sampling device includes a capnographic sensor capable of generating signals indicative of $CO_2$ gas concentration during endoscopic use, and wherein the capnographic sensor includes an infrared LED light associated with an infrared detector, and a reference light emitter associated with a reference light detector.

2. The endoscopic system of claim 1, wherein the capnographic sensor measures $CO_2$ concentration by IR spectroscopy.

3. The endoscopic system of claim 1, wherein the distal end portion of the endoscopic probe includes a distal-most end face, and wherein the sampling device is positioned adjacent the distal-most end face of the endoscopic probe.

4. The endoscopic system of claim 3, wherein the capnographic sensor includes an elongate sampling chamber, and wherein the distal-most end face of the elongate sampling chamber is a aligned with the distal-most end face of the endoscopic probe.

5. The endoscopic system of claim 1, further comprising a control console, the control console receiving signals from the capnographic sensor, processing the received signals, and displaying results of the processed signals.

6. The endoscopic system of claim 5, wherein the control console includes an alert device for generating an alert signal indicative of patient distress based on the received signals from the capnographic sensor.

7. The endoscopic system of claim 6, wherein the alert signal is either visual or audible.

8. The endoscopic system of claim 1, further comprising a respiration sensor.

9. The endoscopic system of claim 8, wherein the respiration sensor generates signals indicative of breath cycles.

10. An endoscopic system, comprising:
an endoscopic probe routable through a passageway of a body, the endoscopic probe having a proximal end, a distal end, and an elongate working channel therebetween, wherein the elongate working channel includes at least one of an illumination system or a visualization system, and wherein at least a distal end portion of the endoscopic probe is configured for insertion into a natural orifice of a body and routable through a tortuous natural lumen of the body; and
a sampling device coupled to the endoscopic probe and having a capnographic sensor capable of generating signals indicative of respiratory gas concentrations during endoscope probe use; said capnographic sensor located at a position proximate the distal end portion of the endoscopic probe such that the capnographic sensor is configured for insertion into the body, and wherein the capnographic sensor includes an infrared LED light associated with an infrared detector, and a reference light emitter associated with a reference light detector.

11. The endoscopic system of claim 10, wherein the distal end portion of the endoscopic probe includes a distal-most end face, and wherein the sampling device is located at the distal-most end face of the endoscopic probe.

12. The endoscopic system of claim 11, wherein the capnographic sensor includes an elongate sampling chamber, and wherein the distal-most end face of the elongate sampling chamber is a aligned with the distal-most end face of the endoscopic probe.

13. The endoscopic system of claim 10, further including a control console functionally connected to the endoscopic probe and the capnographic sensor, the control console receiving at least the generated signals from the capnographic sensor, processing the received signals, and outputting the processed signals for display, wherein the control console includes an alert device for generating a signal indicative of patient distress based on the received signals from the capnographic sensor.

14. The endoscopic system of claim 13, wherein patient distress is determined by comparing the processed signals from the capnographic signals with a value stored in or generated by the control console.

15. The endoscopic system of claim 10, further including a control console functionally connected to the endoscopic probe and the capnographic sensor, the control console receiving at least the generated signals from the capnographic sensor, processing the received signals, and outputting the processed signals for display, wherein the control console receives signals from the capnographic sensor and other signals associated with the body.

16. The endoscopic system of claim 15, wherein the other received signals are respiration signals indicative of breath cycles.

17. An endoscopic system, comprising:
an endoscopic probe, the endoscopic probe including a working channel configured to route an imaging or light system, and wherein at least a distal end portion of the endoscopic probe is configured for insertion into an esophagus of a body and routable through the esophagus of the body; and
a sampling device attached to the endoscopic probe including a capnographic sensor capable of generating signals indicative of respiratory gas concentrations during endoscope probe use; said capnographic sensor located at a position proximate the distal end portion of the endoscopic probe such that the capnographic sensor is configured for insertion into the esophagus of the body, and wherein the capnographic sensor includes an infrared LED light associated with an infrared detector, and a reference light emitter associated with a reference light detector.

* * * * *

UNITED STATES PATENT AND TRADEMARK OFFICE
CERTIFICATE OF CORRECTION

PATENT NO. : 7,967,759 B2  Page 1 of 1
APPLICATION NO. : 11/336688
DATED : June 28, 2011
INVENTOR(S) : Lucien Alfred Couvillon, Jr.

It is certified that error appears in the above-identified patent and that said Letters Patent is hereby corrected as shown below:

Claim 4, col. 9, line 14, "chamber is a aligned" should read --chamber is aligned--.

Claim 12, col. 10, line 6, "chamber is a aligned" should read --chamber is aligned--.

Signed and Sealed this
Thirteenth Day of September, 2011

David J. Kappos
*Director of the United States Patent and Trademark Office*